(12) United States Patent
Gosnet-Haghiri et al.

(10) Patent No.: US 8,747,604 B2
(45) Date of Patent: Jun. 10, 2014

(54) METHOD FOR MANUFACTURING A MICROFLUIDIC CHIP, AND RELATED CHIP AND PLATE

(75) Inventors: Anne-Marie Gosnet-Haghiri, Sceaux (FR); Clément Nanteuil, Issy les Moulineaux (FR)

(73) Assignees: Centre National de la Recherche Scientifique (CNRS) (FR); Universite Paris-Sud 11 (FR)

( * ) Notice: Subject to any disclaimer, the term of this patent is extended or adjusted under 35 U.S.C. 154(b) by 0 days.

(21) Appl. No.: 13/700,606

(22) PCT Filed: May 24, 2011

(86) PCT No.: PCT/EP2011/058496
§ 371 (c)(1),
(2), (4) Date: Nov. 28, 2012

(87) PCT Pub. No.: WO2011/147842
PCT Pub. Date: Dec. 1, 2011

(65) Prior Publication Data
US 2013/0071305 A1   Mar. 21, 2013

(30) Foreign Application Priority Data
May 28, 2010  (FR) ..................... 10 54183

(51) Int. Cl.
| C09J 7/02 | (2006.01) |
| B32B 7/00 | (2006.01) |
| B32B 37/00 | (2006.01) |
| B32B 9/04 | (2006.01) |
| B01L 3/00 | (2006.01) |
| G01N 1/28 | (2006.01) |

(52) U.S. Cl.
USPC ........ 156/329; 422/502; 422/503; 156/272.6; 428/209; 428/447; 428/448

(58) Field of Classification Search
USPC ........................ 422/502–503; 156/272.6, 329
See application file for complete search history.

(56) References Cited

U.S. PATENT DOCUMENTS

2003/0134136 A1 * 7/2003 Biscotto et al. ............... 428/472
(Continued)

FOREIGN PATENT DOCUMENTS

| EP | 2096445 A1 * | 9/2009 | ............... B81C 3/00 |
| WO | 2004048254 A1 | 6/2004 | |

OTHER PUBLICATIONS

Hansen et al., "Fast prototyping of injection molded polymer microfluidic Chips", Journal of Micromechanics & Microengineering, Institute of Physics Publishing. Bristol, GB, vol. 20. No. 1, Jan. 1, 2010. p. 15020, XP02016888.
French Preliminary Search Report for Application No. FR1054183 dated Sep. 22, 2010.

(Continued)

*Primary Examiner* — Bobby Ramdhanie
*Assistant Examiner* — Jennifer Wecker
(74) *Attorney, Agent, or Firm* — Lerner, David, Littenberg, Krumholz & Mentlik, LLP

(57) ABSTRACT

The invention relates to a method for manufacturing a microfluidic chip, wherein said method comprises the steps of: providing a plate combined with a layer of inorganic silica gel of formula: $(HsiO_{3/2})_{2n}$ where n is an integer, and providing a lid; chemically activating the layer of silica gel and the lid, in order to make the layer of gel and the lid hydrophilic; mechanically combining the layer of gel and the lid to form a chip, such that the layer of gel forms an intermediate layer between the plate and the lid; annealing the chip, such that the layer of silica gel transforms into an intermediate layer made up of a $SiO_2$ matrix for rigidly securing the plate to the lid. The invention also relates to a related chip and plate.

11 Claims, 7 Drawing Sheets

(56) References Cited

U.S. PATENT DOCUMENTS

2009/0269767 A1* 10/2009 Soderlund et al. ............... 435/6
2010/0111770 A1    5/2010 Hwang et al.
2012/0003813 A1*  1/2012 Chuang et al. ............... 438/458

OTHER PUBLICATIONS

International Search Report for Application No. PCT/EP2011/058496 dated Sep. 28, 2011.

* cited by examiner

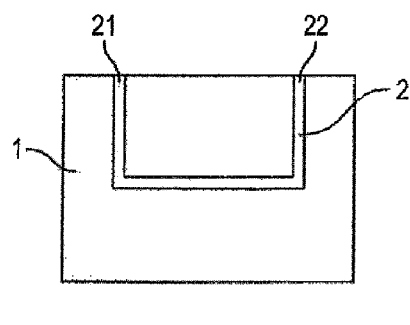
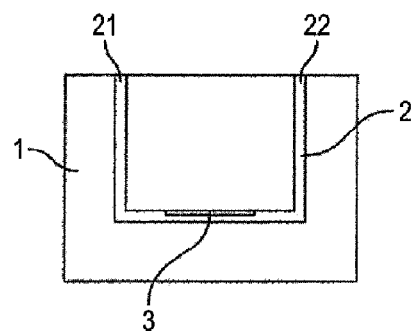
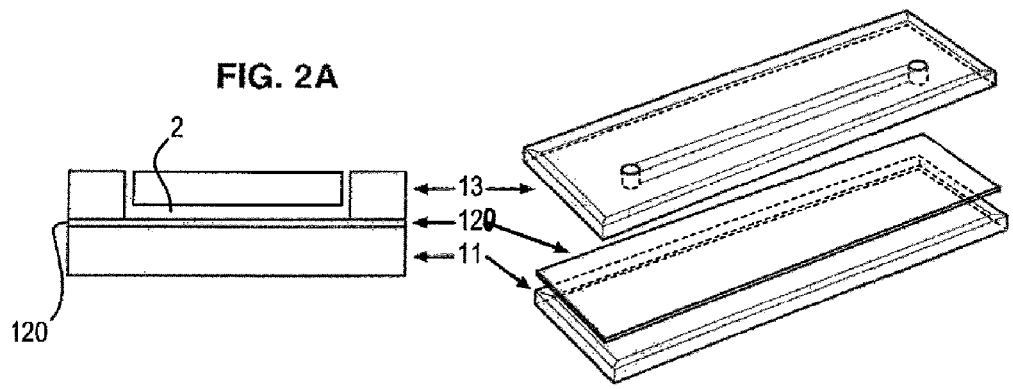

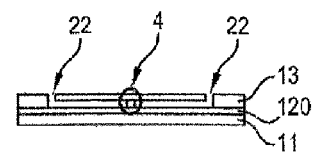
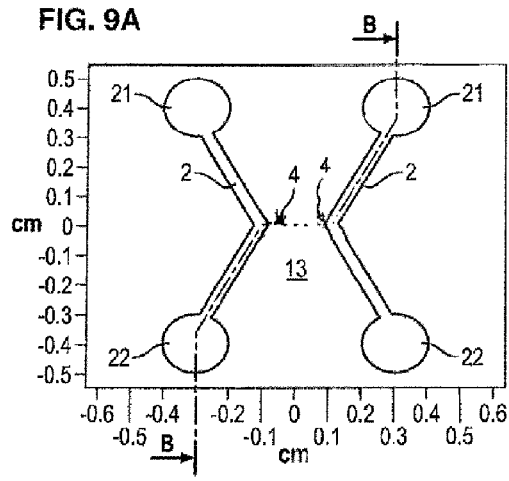
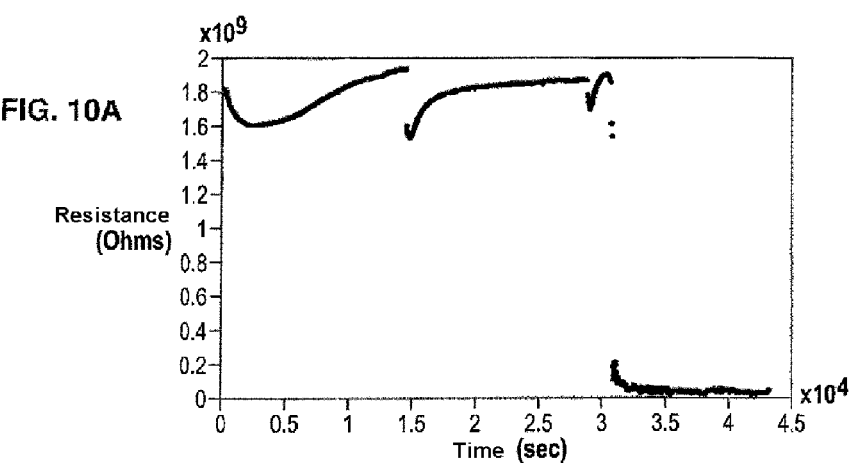
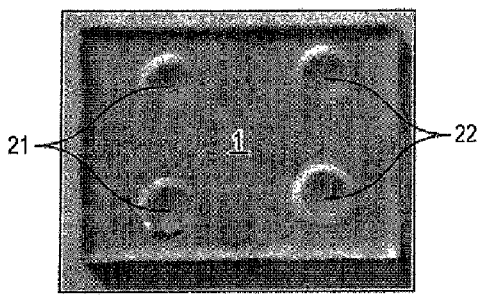

METHOD FOR MANUFACTURING A MICROFLUIDIC CHIP, AND RELATED CHIP AND PLATE

CROSS REFERENCE TO RELATED APPLICATIONS

The present application is a national phase entry under 35 U.S.C. §371 of International Application No. PCT/EP2011/058496, filed on May 24, 2011, which claims priority from French Patent Application No. 1054183 filed on May 28, 2010, the disclosures of which are incorporated by reference herein.

GENERAL TECHNICAL FIELD

The present invention relates to a microfluidic chip comprising a plate and a cap comprising at least one microfluidic channel.

The invention also relates to an associated production process and a plate.

PRIOR ART

As FIG. 1 show, a known microfluidic chip (also called "laboratory on chip" or 'lab-on-a-chip' after English terminology sometimes used by the person skilled in the art) is a device for biological or chemical analysis, which comprises at least one miniaturised plate 1 of minimal thickness (of the order of a few tens to a few hundreds of micrometers), constituted for example by
- glass (that is, a substance which is hard, brittle and transparent, vitreous in structure, essentially formed from alkaline silicates),
- plastic (that is, material constituted by macromolecules obtained by polymerisation or polycondensation and generally having the property of being moulded or modelled), or
- silicon or silica (silicon oxide), on which is etched at least one microchannel 2 (whereof the opening has a diameter of the order of a micrometer) or a nanochannel 2 (whereof the opening has a diameter of the order of a hundred nanometers) which uses any means possible to convey fluids of a sample via an input 21 to different reservoirs or different sensors 3, arranged for analysis of fluids or molecules contained in the sample, the fluid then escaping via output 22.

Microfluidic chips have a multitude of fields of application, such as for example:
- biotechnology, including especially proteomics and genomics;
- biomedicine, including especially the analytical study of separations on chip for early diagnosis of diseases, or for a sort of nanodrugs, for example;
- ecology, toxicology (concerning the quality of food, water, or air for example) or agriculture, fields for which there is a health issue, in particular with respect to the impact of nanoparticles and ions (for example heavy metals) in daily life; and
- pharmacology for in-situ synthesis of novel drugs.

It is understood that all these fields of application are based on biological analysis or chemical analysis in the microfluidic chip, that is, being carried out in fluid volumes under a liter ($10^{-6}$ L), in a confined and perfectly controlled microscopic environment formed by the chip.

Several production techniques of a microfluidic chip comprising glass or silicon are known.

The first known technique consists of making a chip all glass, obtained by a melting process at very high temperature, that is, at a temperature above the vitreous transition temperature Tv, that is, the temperature at which the material transitions from the hard solid state to the viscous or rubbery state—for example for glass based on aluminosodic borosilicate (known for example by the brand name Pyrex):

$$Tv \approx 700° C.$$

or for silica:

$$Tv \approx 1410° C.$$

Reference is made advantageously to the publication by S. C. Jacobson and al, Anal. Chem. 67 (1995), p. 2059-2063 concerning this first technique.

The second known technique, disclosed especially by U.S. Pat. No. 6,129,854, consists of making a chip comprising glass elements stuck in a soda bath. Compared to the first technique, the production temperature is very low, since it is under 100° C.

The third technique consists of making a chip comprising glass elements stuck by means of polymer adhesion (and therefore organic, comprising carbon atoms) for sealing at ambient temperature. Existing glues for glass are generally sol-gels which adhere to glass due to the presence of a vitrification initiator. Reference is made advantageously to the following publications for the principle of sol-gels:
- J-P. Boilot, M. Canva, C. Sanchez, B. Lebeau, F. Chaput, Y. Levy, J. Zyss, Applications of hybrid materials in the field of optics, Hybrid materials, Arago series, French Observatory for Advanced Technologies (Masson), 17, 181, 1996; and
- F. Chaput, J. P. Boilot, F. Devreux, M. Canva, A. Brun and P. Georges, Gels for optics, for Science, September 1993, pp. 46-53.

The fourth technique consists of making a chip comprising glass elements having a sodium-based ($Na_2O$) flux, welded anodically by means of a fine semiconducting layer of amorphous silicon (aSi—H). This technique consists of creating covalent bonds between the glass and the fine semiconducting layer, under the simultaneous action of a strong electrical field (from several hundreds to several thousands of volts per centimeter) and a moderate temperature (typically up to 450° C. maximum). An insulating layer of some tens of nanometers is created and ensures mechanical cohesion to the interface between the glass and the semiconducting layer.

These techniques have disadvantages, however.

The first technique is costly in terms of energy and impossible to execute when the chip contains fine nanostructures (for example, glass nanochannels 2, of size less than 40 nm), due to creep of the glass at very high temperature, consequently causing the destruction of nanostructures.

The integration of circuits 3 is also almost impossible, since they are limited to materials of a very high melting point (above Tv of the glass constituting the chip).

The use of production tools having a dilation coefficient below that of glass and supporting the very high production temperature is also necessary.

Also, the use of the solder in the second production technique is difficult for production of a chip integrating either micro/nanostructures or circuits with several materials, and makes it almost impossible to carry out industrially.

The carbon adhesive obtained by the third technique has low chemical inertia, low mechanical resistance and low electrical insulation (because it is organic material) associated with low breakdown tension of the adhesive.

The fourth production technique has the advantage of substantially lowering the production temperature which varies between 100° C. and 450° C. as a function of the electrical potential applied as well as a function of the adhesion time. However, the final properties of the chip are very degraded relatively to an all-glass chip such as that obtained by the first technique.

Electrical insulation in the chip is not in fact of such good quality as for all-glass chips: the lateral walls of conductive amorphous silicon (a-Si) of the channels are put in contact with the sample circulating in the chip. Parasite electrochemical reactions can therefore take place in some cases.

In addition, cracking zones are not rare at the interface where exposing of the intermediate layer leads to the same degradations as those due to the abovementioned parasite electrochemical reactions.

Finally, the integrated circuits in the chip can be degraded by the electrical field necessary for production of the chip.

In extreme conditions of use, the chips have a very limited shelf life of the order of a few hours.

Low-temperature production techniques of microfluidic chips comprising polymer material in place of glass or silica are also known, such as for example polydimethylsiloxane (PDMS) or methyl polymethacrylate (PMMA).

The production technique is relatively straightforward, as adhesion of the elements composing the chip occurs at ambient temperature and is followed by simple degassing annealing.

The integration of circuits 3 in the chip is also made easy.

Chips mainly comprising polymer material however also have disadvantages.

The polymers used are in fact always porous, and mechanically too deformable to integrate nanostructures of dimensions under 100 nm (their lowest Young's modulus engenders deformations relative under considerable stress).

Finally, chips made of material polymer are not very chemically stable over time. This poor chemical inertia therefore prohibits any use for fines in extreme ionic media, that is, weakly or very strongly concentrated.

PRESENTATION OF THE INVENTION

The invention proposes rectifying at least one of these disadvantages.

For this purpose, a microfluidic chip is proposed according to the invention, comprising
a plate, and
a cap comprising at least one microfluidic channel,
characterised in that it further comprises a single intermediate layer between the plate and the cap, formed by an inorganic $SiO_2$ matrix.

The invention is advantageously completed by the following characteristics, taken singly or in any technically possible combination:
the layer has a thickness of between 100 nm and 10 μm, and preferably of between 300 nm and 400 nm;
the chip comprising at least one circuit in the cap; and/or at least one circuit on the cap, connected to the cap by an inorganic $SiO_2$ matrix.

The invention also relates to a production process and associated plate.

Therefore, the invention also relates to a production process of a microfluidic chip, characterised in that it comprises the steps of:
providing a plate connected to a layer of gel of inorganic silica of formula:

$(HSiO_{3/2})_{2n}$ where n is a natural whole number, and providing a cap;
chemical activation of the layer of silica gel and of the cap to make the layer of gel and the cap hydrophilic;
mechanical association of the layer of gel and of the cap to form a chip such that the layer of gel forms an intermediate layer between the plate and the cap;
annealing of the chip such that the layer of silica gel is transformed into an intermediate layer formed by an $SiO_2$ matrix connecting the plate and the cap.

The process is advantageously completed by one or more of the following characteristics:
the maximal annealing temperature Tr of the chip (1) is such that:

$$20° C. < Tr < Min(Tv_{plate}, Tv_{cap})$$

where Min is the minimum mathematical operator, and $Tv_{plate}$ and $Tv_{cap}$ are respectively the vitreous transition temperature of the plate and the vitreous transition temperature of the cap;
the maximal annealing temperature Tr of the chip is such that:

$$100° C. \leq Tr \leq 450° C.$$

the annealing temperature evolves, during the annealing step, from 20° C. to Tr at a speed of a few degrees Celsius per minute to allow transformation without cracking of the silica gel in the $SiO_2$ matrix;
the chemical activation step of the layer of silica gel occurs due to Air/$O_2$ plasma; and the chemical activation step of the cap takes place due to a bath of ammonia or sulphuric acid to enable formation of —OH chemical groups at the surface of the gel and of the cap;
the inorganic gel is gel of inorganic of formula:

$(HSiO_{3/2})_{2n}$ where n is a natural whole number
the process comprises a step of:
formation of at least one microfluidic channel in the cap; and/or
formation of at least one circuit in the cap; and/or
association of at least one circuit on the cap due to a stratum of chemically activated silica gel, prior to the step of mechanical association of the gel and of the cap.

The plate and the cap are preferably made of glass, for example glass based on aluminosodic borosilicate (known for example under the brand name Pyrex).

The use of a layer of gel of inorganic silica (that is, comprising no carbon atom) is novel, as it differs from all existing adhesives for glass. The gel of inorganic silica comprises no vitrification initiator.

The invention has numerous advantages.

It allows the production of a chip having a structure similar to chips entirely made of glass-type material.

When the plate and the cap are made of glass, the chip according to the invention benefits totally from the exceptional properties of glass, specifically:
high optical transparency for clear observation,
high mechanical resistance, exhibiting a high Young's modulus and high breaking resistance (as a function of the type of glass used);
low porosity, which makes the chip perfectly adapted to chemical analysis applications in conditions of very low concentration (analysis of weakly concentrated toxins, for example) which avoid any pollution from the exterior of the chip and any leakage of dangerous products to the exterior;

chemical inertia to the majority of chemical compounds (with the exception of derivatives of hydrofluoric acid). Various chemical solutions can therefore be circulated in the microchannels. For example, the surfaces of the fluidic channels are naturally hydrophilic as a result of chemical treatments carried out for production of the chip. This specificity is important for analysis of biological samples. Yet, if necessary, it is also possible to treat the fluidic channels to make them hydrophobic by circulation of an adapted solution. Finally, the chip can undergo chemical cleaning and can be biopassivated at the surface by simple circulation of adapted liquid known to the person skilled in the art to freely obtain biocompatibility. The advantage of the chemical inertia character of the chip is clear here;

considerable electrical insulation which especially allows correct operating of the circuits and the application of strong external electrical fields (as in the case of capillary electrophoresis on chip for example).

A chip according to the invention can consequently be used for analysis and follow-up of dangerous biological and chemical compounds either in solution or in gaseous form.

A chip according to the invention has a multitude of fields of application, such as for example:

biotechnology, including especially proteomics and genomics;

biomedicine, including especially the analytical study of separations on chip for early diagnosis of diseases (glucometers for example), or for a sort of nanodrugs for example, as well as controlled diffusion of drugs;

ecology, toxicology (concerning the quality of food, water, or air for example) or agriculture, fields for which there is a health issue, in particular with respect to the impact of nanoparticles and ions (for example heavy metals) in daily life; and pharmacology for in-situ synthesis of novel drugs.

When it comprises nanochannels or nanoslots, it can be subjected to a strong electrical field to concentrate biomolecules or proteins in the nanochannels or the nanoslots, for the formation of biological filters on even very small particles, for example for the treatment of water, or for the production of hydrogen by dissociation of water.

The relatively low production temperature of a chip according to the invention permits association of glass with materials which do not support high temperatures and therefore increases the choice of materials which can be associated with glass in the chip.

The relatively low production temperature reduces energy production costs of each chip.

A chip according to the invention is mechanically and chemically stable over a period of several months, even after exposure to electrophoresis under strong electrical field and in extreme pH conditions. A chip according to the invention can be used several times.

A chip according to the invention can comprise three layers, which easily integrates nanostructures, sensors or circuits in one of the layers forming the chip.

PRESENTATION OF THE FIGURES

Other characteristics, aims and advantages of the invention will emerge from the following description which is purely illustrative and non-limiting, and which must be considered in conjunction with the attached diagrams, in which:

FIG. 1A, already commented on, illustrates a longitudinal section of a known microfluidic chip;

FIG. 1B, already commented on, illustrates a longitudinal section of a known microfluidic chip comprising a circuit;

FIG. 2A shows a longitudinal section of a microfluidic chip according to the invention;

FIG. 2B shows an exploded view of a microfluidic chip according to the invention;

Figure 3:
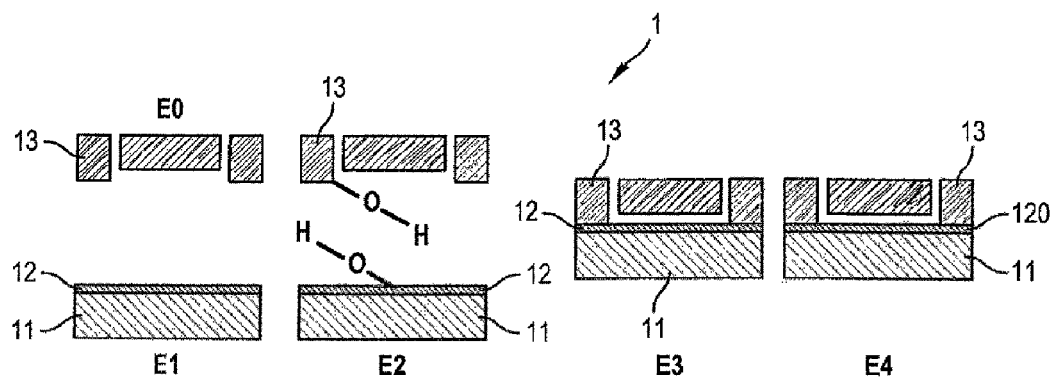
Figure 4:
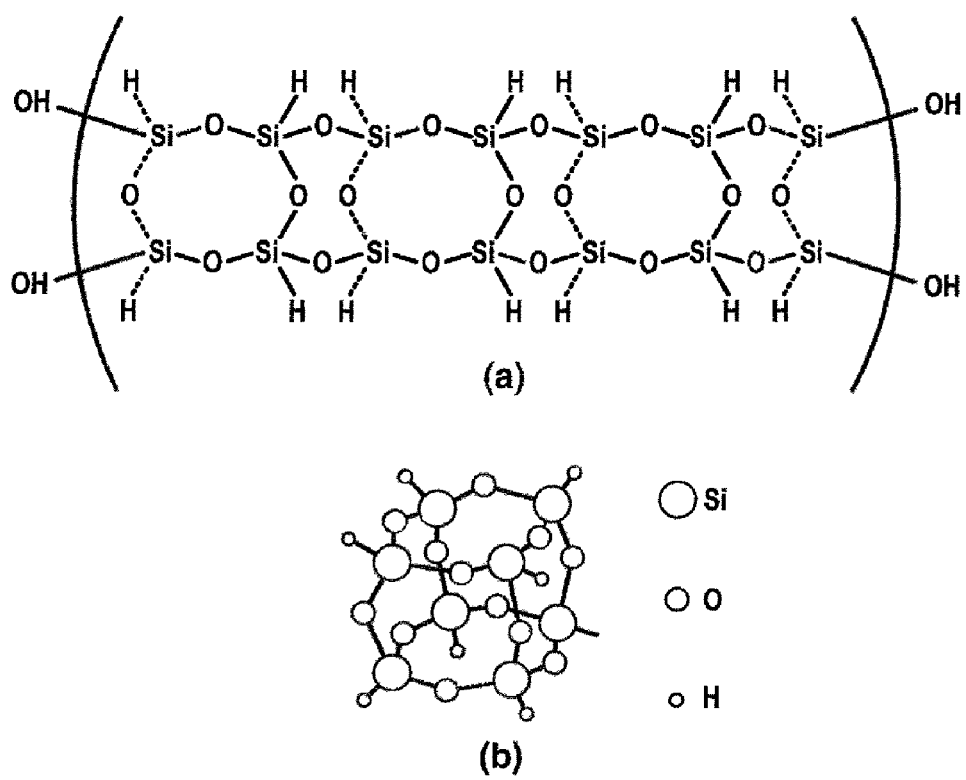
Figure 5:
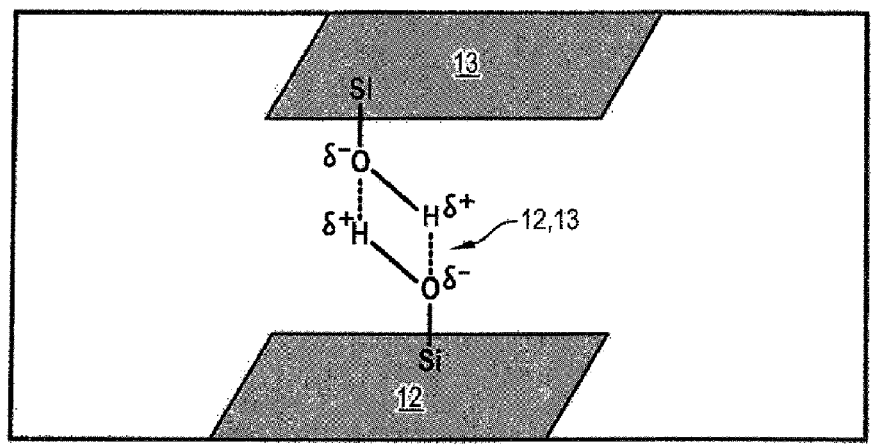
Figure 6:
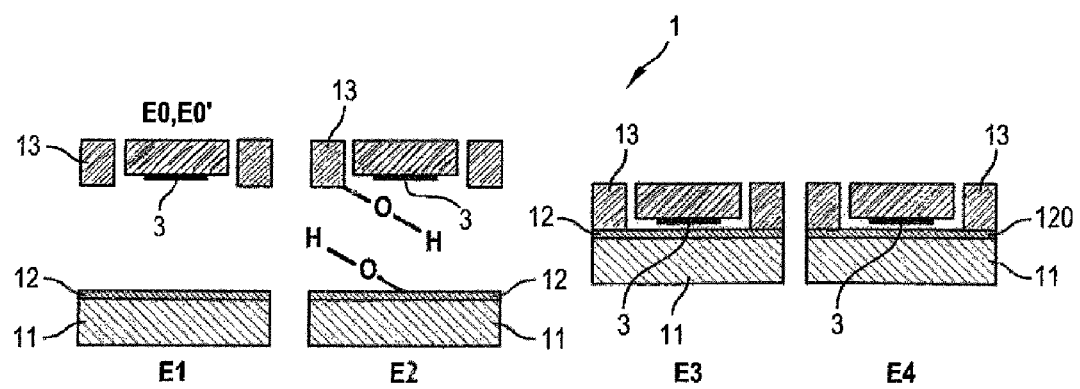
Figure 8:
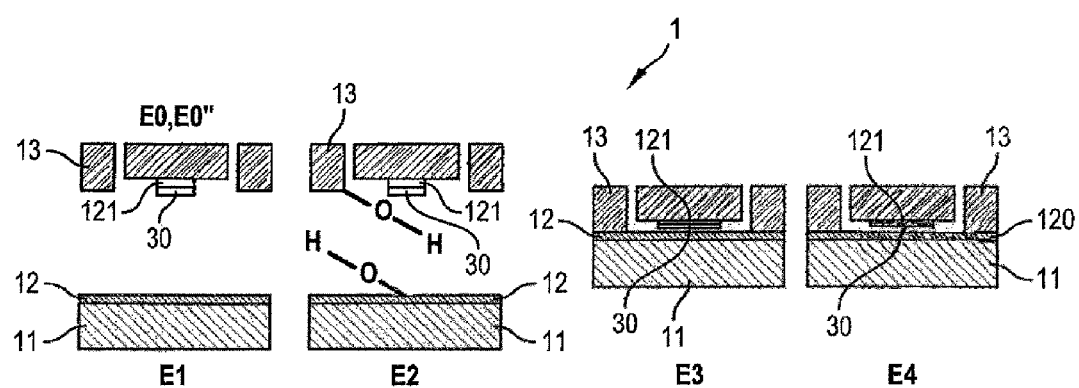

FIG. 3 schematically shows the principal steps of a possible production process of a chip according to FIG. 2;

FIG. 4 schematically show possible molecular configurations for a gel of inorganic silica utilisable in the invention;

FIG. 5 schematically illustrates the formation of hydrogen bonds, especially between the layer of gel of inorganic silica and the cap;

FIG. 6 schematically shows the principal steps of a possible production process of a chip according to the invention comprising a circuit;

FIGS. 7A-G schematically show different examples of circuits according to FIG. 6;

FIG. 8 schematically shows the principal steps of a possible production process of a chip according to the invention comprising a circuit connected by adhesion;

FIG. 9A illustrates a plan view of a chip comprising two channels;

FIG. 9B schematically illustrates a sectional view of a chip according to FIG. 9A; and FIG. 10A illustrates the evolution of the electrical resistance of the chip according to FIG. 9, FIG. 10B showing that the chip undergoes no degradation in extreme conditions.

In all the figures, similar elements bear identical reference numerals.

DETAILED DESCRIPTION

FIG. 3 schematically shows the principal steps of a possible production process of a microfluidic chip 1 according to the invention, represented schematically in FIGS. 2A and 2B.

A possible production process of the microfluidic chip 1 comprises the following principal steps.

A step E1 consists of providing a plate 11 connected to a single layer 12 of gel of inorganic silica and providing a cap 13.

The plate 11 and the cap 13 can be of any type of material, such as for example glass (that is, a hard substance, brittle and transparent, of vitreous structure, essentially formed by alkaline silicates), plastic material (that is, material constituted by macromolecules obtained by polymerisation or polycondensation and generally having the property of being moulded or modelled), or silicon or silica.

The plate 11 and the cap 13 are preferably made of glass, for example glass based on aluminosodic borosilicate (known for example by the brand name Pyrex).

The layer 12 of silica gel comprises a gel of inorganic silica, comprising no carbon atom, of general formula:

$$(HSiO_{3/2})_{2n} \tag{F1}$$

where n is a natural whole number greater than or equal to 1.

Chemical compounds of formula F1 are commonly called hydrogen silsesqioxane or HSQ (Hydrogen SilsesQuioxane) by the person skilled in the art.

HSQs have a low dielectrical constant, which gives them electrical insulation properties as disclosed in the article by Balkhanov in Phyl. Trans. R. Soc. A (2006) 364, p. 201.

Examples of HSQ which can be utilised for the invention are illustrated schematically in FIG. 4.

FIG. 4A illustrates a substantially plane HSQ configuration (in English "ladder HSQ") disclosed for example in the article by Albrecht and Blanchette, in the journal "Journal of the Electrochemical Society" appearing in 1998, No. 145, pp. 4019-4025, and sold by the company Tokyo Ohka Kogyo.

FIG. 4B illustrates a cage HSQ configuration, for example sold under the brand name FOX15 by the company Dow Corning, with $$n=4$$

in the formula F1.

Other usable HSQ are known for example from the article by Frye and Collins appearing in the journal "Journal of the American Chemical Society" in 1970, No. 92, p. 5586 and following. This article discloses especially other HSQ oligomers according to the formula F1 with $$n=4,5,6,7 \text{ or } 8$$

for example.

During the association step of the layer 12 of gel to the plate 11, the gel is deposited on the plate 11 by centrifugation, for example by coating on spinner. It is evident that vaporisation of the gel on the plate 11 would also be possible.

On completion of step E1 a plate 11 connected to a layer 12 of gel of inorganic silica for the formation of a chip 1 according to the invention is therefore obtained.

Without chemical activation, the layer 12 of gel of inorganic silica does not have the least adherence to the plate 11 or to the cap 13, especially when they are made of glass.

For this reason, the process comprises a step E2 of chemical activation of the layer 12 of silica gel and of the cap 13 to make the layer 12 of gel and the cap 13 hydrophilic, which will produce some adherence of the layer 12 to the cap 13, as will be evident later on.

The activation step of the layer 12 of gel is conducted by oxygen plasma which ensures the presence of —OH groups at the surface, as evident from FIG. 3, ensuring its hydrophilic character.

The activation step of the cap 13 is performed by a conventional activation process which produces —OH groups at the surface, ensuring its hydrophilic character. It consists for example of immersing the cap 13 in a $H_2O/NH_4OH/H_2O_2$ bath for an hour at 70° C./80° C. This process is disclosed for example in the publication by Bhattacharya et al, in "Applied Surface Science", published in 2007, No. 253, pp. 4220-4225.

The cap 13 can also be dipped in a bath of sulphuric acid for example.

The process also comprises a step E3 of mechanical association of the layer 12 of gel and of the cap 13 to form a chip 1 such that the layer 12 of gel forms a single intermediate layer between the plate 11 and the cap 13.

During step E3, due to the fact that the layer 12 of gel and the cap 13 are hydrophilic, there is formation of hydrogen bonds 1213 (also called "H bonds" or "Van der Walls bonds" by the person skilled in the art) between the layer 12 of gel of inorganic silica and the cap 13, as shown schematically in FIG. 5.

The hydrogen bonds obtained during step E3 permit molecular adhesion, by bridging of the hydrogen bonds. The resulting molecular adhesion is similar to adhesion obtained at high temperature according to the first technique described in the prior art, whereas the process according to the invention uses only one layer 12 of gel of inorganic silica which does not comprise a vitrification initiator.

Molecular adhesion takes place at ambient temperature, or 20° C.

The process further comprises an annealing step E4 of the chip 1 such that the single layer 12 of silica gel is transformed into an intermediate layer 120, formed by a $SiO_2$ connecting matrix of the plate 11 and of the cap 13. During annealing, the hydrogen bonds 1213 are transformed into covalent bonds, that is, bonds between atoms per pair of electrons.

The maximal annealing temperature Tr of the chip 1 is such that:

$$20° C. < Tr < \mathrm{Min}(Tv_{plate}, Tv_{cap})$$

where Min is the minimum mathematical operator, and $Tv_{plate}$ and $Tv_{cap}$ are respectively the vitreous transition temperature of the plate 11 and the vitreous transition temperature of the cap 13.

Such an annealing temperature Tr permits transformation of the gel of inorganic silica into an $SiO_2$ matrix, avoiding the creep of the plate 11 and of the cap 13.

In the event where the plate 11 and the cap 13 are made of glass, for example glass based on alum inosodic borosilicate, $$Tv_{plate} = Tv_{cap} = 700° C.$$

In this case, the maximal annealing temperature Tr of the chip 1 is preferably such that:

$$50° C. \leq Tr \leq 600° C.,$$

and very preferably such that:

$$100° C. \leq Tr \leq 450° C.$$

Advantageously, $$150° C. \leq Tr \leq 300° C.$$

The chip 1 can therefore be qualified as a "trilayer" chip, a first layer comprising the plate 11, a second layer comprising the intermediate layer 120, and a third layer comprising the cap 13.

When the plate 11 and the cap 13 are made of glass, the resulting trilayer chip has physico-chemical characteristics equivalent to those of chips made of glass obtained according to the first technique of the prior art.

However, given that the intermediate layer 120 formed from silica gel is perfectly insulating, the chip has electrical qualities similar to an all-glass chip, even if the plate 11 comprises a material other than glass.

In all cases, the chip according to the invention is obtained with a production temperature less than the vitreous transition temperature of the plate 11, and less than the vitreous transition temperature of the cap 13. The production energy cost is therefore less than in the prior art.

In addition, because the maximal annealing temperature Tr is less than the minimal vitreous transition temperature of the plate 11 and of the cap 13, the process can comprise a step E0 for formation of at least one microfluidic channel 2 in the cap 13, prior to the mechanical association step of the gel 12 and of the cap 13, and therefore annealing. The microchannel 2 will not deteriorate during annealing step E4.

The cap 13 advantageously comprises at least one microfluidic channel 2, and especially one channel 2 whereof the opening has a diameter of less than 100 nm, for example 40 nm. The nanostructures of the channel 2 will not in fact be affected by the annealing at a preferred temperature under 300° C.

The formation of the channel 2 in the cap 13 presents no difficulty for the person skilled in the art, and is not described in any further detail here for the sake of clarity and concision. Each channel 2 is for example obtained by the use of sulphuric acid, ammonia (liquid), hydrofluoric acid, and/or obtained by lithography and reactive ionic etching, for example, directly in the material of the cap 13. The channel 2 can be a simple longitudinal channel, in the form of a cross or a Y, but can of course have other forms, and especially can comprise reservoirs, for example in the form of microcavities.

Also, because the temperature Tr is relatively low, the process can comprise a formation step E0' of at least one circuit 3 in the cap 13, as shown in FIG. 6. As previously, step E0' precedes the mechanical association step of the gel 12 and of the cap 13.

The formation of the circuit 3 in the cap 13 utilises conventional microelectronic methods which present no difficulty for the person skilled in the art and is not described in any further detail here for the sake of clarity and concision. The circuits 3 are for example obtained by the use of sulphuric acid, ammonia (liquid), hydrofluoric acid, and/or obtained by lithograph and reactive ionic etching, directly in the material of the cap, these techniques being for example linked to known processes for depositing metals to form electrical tracks (for example for controlling the temperature on the chip 1), or magnetic electrodes by way of non-limiting examples.

The following developments give some possible examples of known circuits.

Sensors for measuring temperature formed by circuits 3 such as mentioned hereinabove are already known, and especially take measurements of temperature in real time.

Figure 7A:
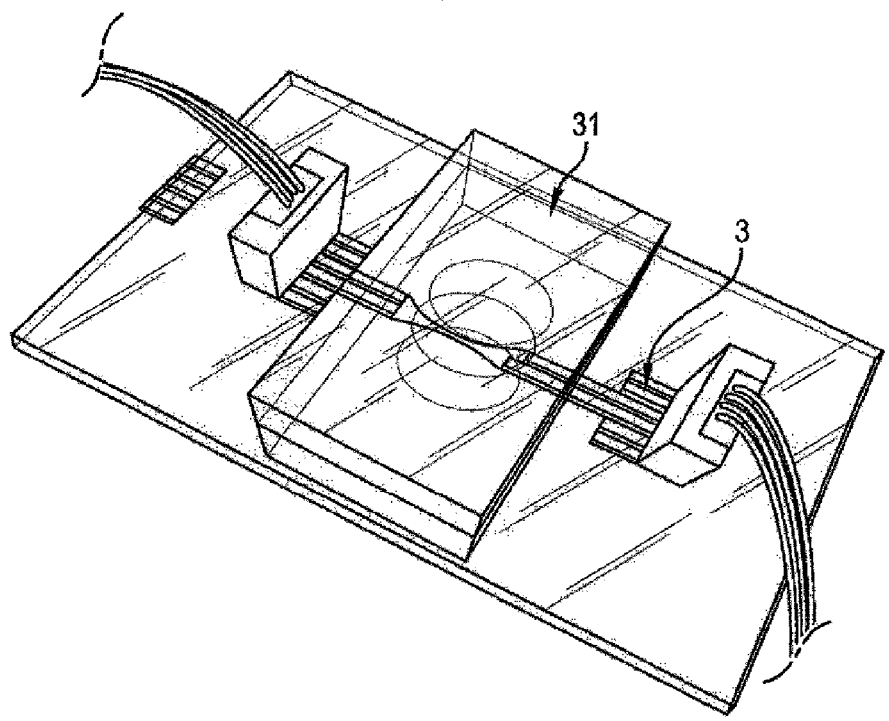
Figure 7B:
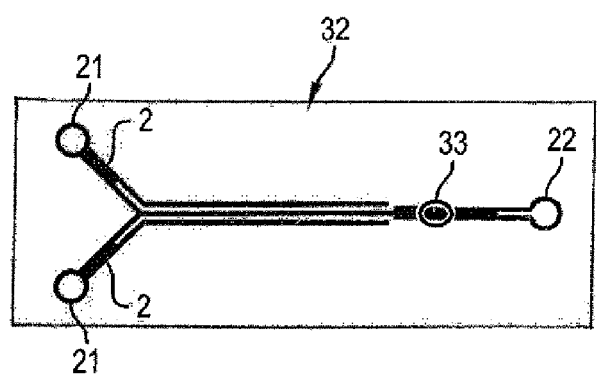

FIG. 7A shows a microconductimeter 31 for measuring nanofluids, comprising a network of metallic electrodes 3. Such a microconductimeter 31 is disclosed for example in the article by G. Velve Casquillas, "Microlectronic Engineering" 84 (2007) p. 1194 to 1197. FIG. 7B illustrates a microcalorimeter 32 coupled to chemical a reaction chamber 33 formed by a Y-shaped channel 2. Such a microcalorimeter 32 is disclosed for example in the article by G. Velve Casquillas, "Microlectronic Engineering" 85 (2008) pp. 1367 to 1369.

Figure 7C:
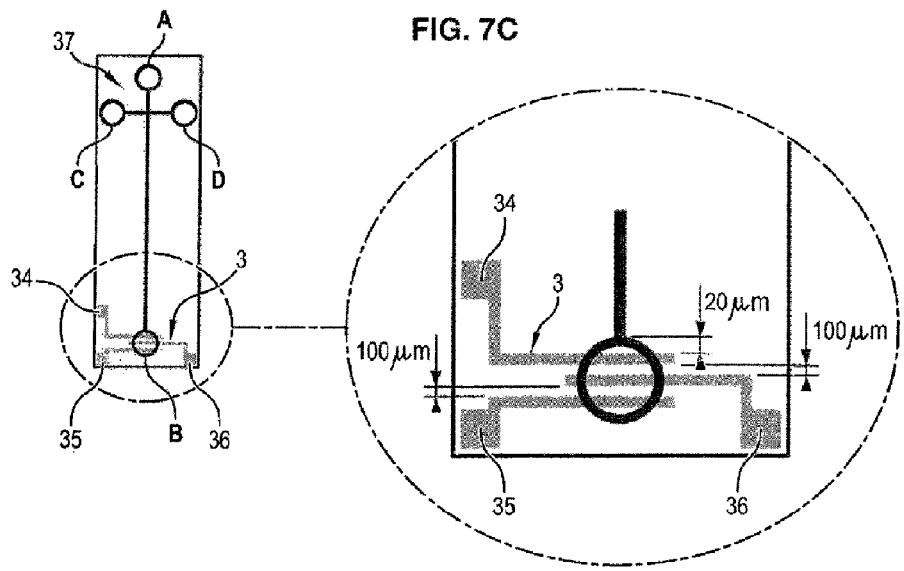
Figure 7D:
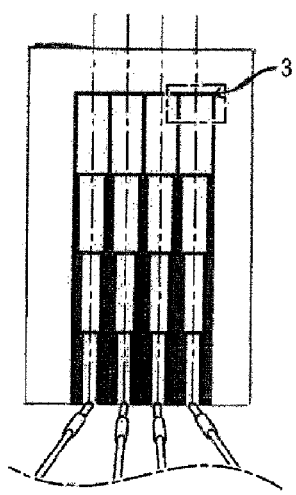

Electrochemical sensors comprising electrodes are also known, as shown in FIGS. 7C and 7D.

In FIG. 7C, the chip 1 can comprise for example a sensor 3 including three microelectrodes 34, 35 and 36 placed downstream of a cross 37 of electrophoretic separation, for electrochemical detection of neurotransmitters of dopamine and epinephrine type. Such a sensor is disclosed for example in the article by Castano-Álvarez, "Talanta" 80 (2009) pp. 24 to 30. The measured electrical signal originating from microelectrodes 34, 35 and 36 can be analysed in compact electronics which can be hosted on the chip. FIG. 7D shows another example of electrodes 3 for electrochemistry integrated in a multiplexed chip comprising a network of thirty-two electrodes, for example for electro-chemoluminescence experiments.

Equivalent electrodes can also be used to take measurements of conductivity of chemical or biological solutions.

Figure 7E:
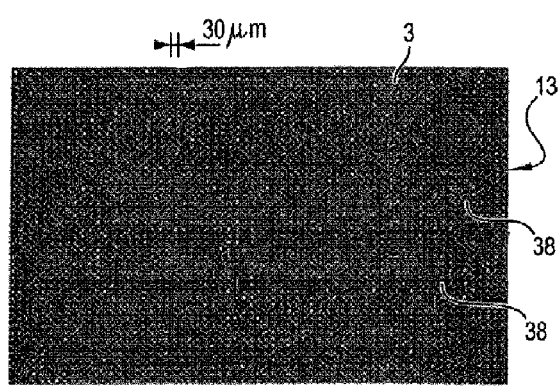

FIG. 7E schematically illustrates photonic nanosensors 38 (resolution of 30 nm) obtained by the technique known as nanoimpression which can be combined with reactive ionic etching methods in multilayer stacks of resin to obtain nanomotifs with very large form factors.

Figure 7F:
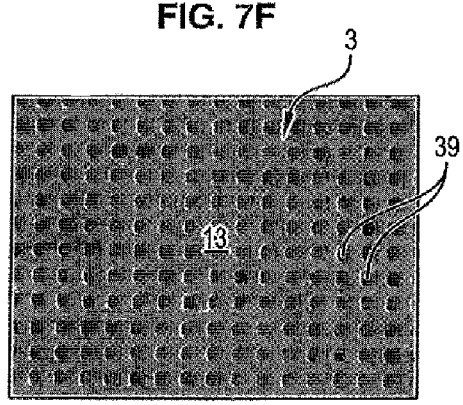
Figure 7G:
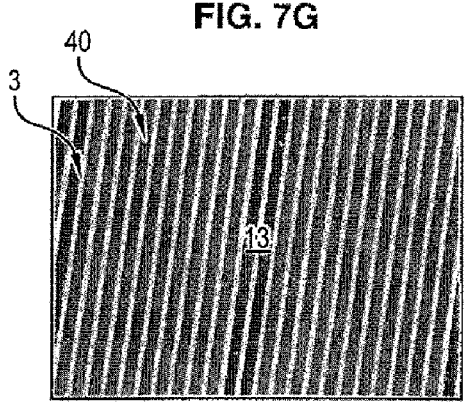

FIGS. 7F and 7G represent networks of known optical trapping nanostructures obtained by the above combination.

FIG. 7F illustrates an example of plasmonic structures 39 (that is, capable of transmitting light signals using electromagnetic waves emitted by collective oscillation of electrons). FIG. 7G illustrates an example of a network 40 of photonic crystal of lines, imprinted in an oxide gel.

As shown in FIG. 8, the process can comprise an association step E0" of at least one circuit 30 on the cap 13 due to a stratum 121 of chemically activated silica gel. The stratum 121 is of identical composition to the layer 12, and is activated chemically in the same way as the layer 12, resulting in molecular adhesion between the circuit 30 and the cap 13, as shown in FIG. 5. During annealing step E4, the stratum 121 will be transformed into a $SiO_2$ matrix in the same way as the intermediate layer 120 at the same time.

The circuit 30 can be any type of sensor available in microelectronics. The circuit 30 can contain nanocircuits, such as for example nanoelectrodes and optical nanostructures.

The adhered circuit 30 can be combined into a circuit 3 and/or a channel 2 such as described earlier.

The formation of the connector associated with the different circuits 3 and 30 for connecting to analysis electronics of signals originating from the circuits 3 or 30 does not pose any difficulty for the person skilled in the art either, and is not described in any further detail here for the sake of clarity and concision.

EMBODIMENT

The following developments give an example for the production of a chip 1.

With respect to step E1 for providing the cap 13, the step E0, E0' and/or E0" is first performed on the cap 13 of
formation of at least one microfluidic channel 2; and/or
formation of at least one circuit 3; and/or
association of at least one circuit 30 by way of a stratum 120 of chemically activated silica gel.

It is evident that the association between the stratum 120 and the cap 13 is identical to the association between the layer 12 and the plate 11 described in the present description: in this way, activation of the stratum 120 is identical to activation of the layer 12 described in the present description, with chemical activation of the cap 13 by bath ammonia.

The plate 11 and the cap 13 have a diameter of around 5 cm (2 inches). Moving up to production of several chips on larger substrates (4 to 10 inches, for example) is easily feasible, by adding a final cutting step. The thickness of the plate 11 and of the cap 13 can be typically between 200 µm and 1 mm. The finer the thickness is, the easier the contact is, but the more fragile are the plate and the cap.

With respect to step E1 for providing the plate 11, to connect the layer 12 and the plate 11, a small quantity (a drop, for example) of an HSQ solution filtered at 0.45 µm is deposited on the plate 11, in turn placed on a spinner. The HSQ solution is filtered to avoid any dust harmful to adhesion.

The HSQ layer 12 is obtained by centrifugation at 5,000 rpm for 30 seconds (fixed acceleration at 2,000 rpm).

The thickness of the layer 12 obtained is generally between 100 nm and 10 µm, typically less than a micrometer, for example between 300 nm and 400 nm.

The plate 11 connected to the layer 12 HSQ is annealed at 150° C. for two minutes on a heating plate.

With respect to step E2, chemical activation of the upper surface of the layer 12 is obtained by immersion of the plate 11 connected to the layer 12 in oxygen-rich plasma (300 mtorr) for 30 seconds.

The cap 13 is as such chemically activated due to immersion in a bath ($NH_3$ (28%)/$H_2O_2$/$H_2O$ 1:1:5) for around one hour at 80° C., then rinsed in deionised water for two minutes. The cap can also be dipped in a bath of sulphuric acid, for example.

Once step E2 is completed, step E3 of mechanical association of the layer 12 and of the cap 13 should be performed relatively rapidly. Ambient hygrometry must not exceed 50% during step E3 to obtain proper adhesion thereafter. Step E3 is conducted advantageously at 20° C.

During step E3, the mechanical association of the layer 12 and of the cap 13 can be done by manual pressing. For large surfaces, a press of the commercially available Nanonex NXR2500 brand name will be used, for example, which applies uniform pressure on the plate 11 and the cap 13, due to a system of two supple membranes.

The association is completed at low pressure (less than 10 bar, or 1 MPa). The pressure to be applied depends on the density of the channel motifs 2 or circuits 3 on the cap 13.

The annealing step E4 is slow. Typically a range of ten hours at 300° C. is necessary to transform the HSQ into a silica matrix.

Annealing takes place in a classic oven, under nitrogen flow of 50 cm³/sec.

During step E4, the annealing temperature evolves from 20° C. to Tr (maximal annealing temperature, specifically the temperature of the range) at a speed of a few degrees Celsius per minute, to enable transformation without cracking of the silica gel in the $SiO_2$ matrix.

So, the speed of evolution of the annealing temperature is
7° C./min
between 20° C. and 200° C.,
5° C./min
between 200° C. and 250° C., and
3° C./min
between 250° C. and 300° C. (Tr), then
300° C. range
over ten hours, and finally slow decrease by turning off the oven heat.

If the preferred mechanical resistance for the chip is lower (mechanical resistance at pressure of a few bars only), it is possible to lower the annealing temperature, for example by carrying out annealing once only at 150° C.

For an annealing temperature Tr of 150° C., a range of twenty hours at 150° C. is preferable, with an evolution speed of
1°/min
between 20° C. and 150° C.

If the preferred mechanical resistance for the chip is lower still, it is possible to diminish the time length of the annealing range, for example by carrying out only one range of ten hours at around 150° C., or even 5 hours only. It is important to finally obtain an $SiO_2$ matrix.

FIGS. 9A and 9B illustrate a chip comprising two bent microchannels 2, one being connected to an anode, the other to a cathode. Each microchannel forms an opening of 2 μm in diameter, and, at the level of their elbow 4 the channels 2 are spaced only by 10 μm by the material of the cap 13 and/or the silica matrix formed by the annealed silica gel. A solution frequently used in biology, specifically a buffer solution, here a phosphate buffer solution (PBS) is fed into each channel 2 (via the input 21 then the output 22) at a concentration of 50 mM with pH of 6.6.

FIG. 10A shows that the chip exhibits no sign of degradation under the application of 1 MVolt/cm through the zone of 10 μm.

FIG. 10B shows that resistance of the chip at an average value of 10^9 Ohms, or resistance of two orders of magnitude greater than chips of the prior art according to the fourth technique, for example. This shows the proof of the insulating character of the intermediate layer 120.

The service life of a chip according to the invention is therefore several months at least.

The invention claimed is:

1. A production process for a microfluidic chip, wherein it comprises the steps of:

providing a glass plate connected to a layer of gel of inorganic silica of formula:

$$(HSiO_{3/2})2_n$$

where n is a natural whole number greater than or equal to 1, and providing a glass cap;

chemical activation of the layer of silica gel and of the cap to make the layer of gel and the cap hydrophilic;

mechanical association of the layer of gel and of the cap to form a chip such that the layer of gel forms an intermediate layer between the plate and the cap;

annealing of the chip such that the layer of silica gel is transformed into an intermediate layer formed by an $SiO_2$ connecting matrix of the plate and of the cap.

2. The process as claimed in claim 1, in which the maximal annealing temperature Tr of the chip is such that:

$$20°\ C. < Tr < Min(Tv_{plate}, Tv_{cap})$$

where Min is the minimum mathematical operator, and $Tv_{plate}$ and $Tv_{cap}$ are respectively the vitreous transition temperature of the plate and the vitreous transition temperature of the cap.

3. The process as claimed in claim 2, in which the maximal annealing temperature Tr of the chip is such that:

$$100°\ C. \leq Tr \leq 450°\ C.$$

4. The process as claimed claim 2, in which the annealing temperature evolves during the annealing step from 20° C. to Tr at a speed of a few degrees Celsius per minute to allow transformation without cracking of the silica gel in the $SiO_2$ matrix.

5. The process as claimed in claim 1, in which
the chemical activation step of the layer of silica gel is conducted due to Air/$O_2$ plasma; and
the chemical activation step of the cap is conducted due to a bath of ammonia or sulphuric acid, to allow the formation of chemical —OH groups at the surface of the gel and of the cap.

6. The process as claimed in claim 1, comprising a step of:
formation of at least one microfluidic channel in the cap; and/or
formation of at least one circuit in the cap; and/or
association of at least one circuit on the cap due to a stratum of chemically activated silica gel, prior to the mechanical association step of the gel and of the cap.

7. A microfluidic chip comprising
a glass plate,
a glass cap comprising at least one microfluidic channel, and an intermediate layer between the plate and the cap, formed by an inorganic $SiO_2$ matrix, the microfluidic chip being characterized in that the layer formed by an $SiO_2$ matrix is obtained by a process as claimed in claim 1.

8. The chip as claimed in claim 7, in which the layer is unique.

9. The chip as claimed in claim 7, in which the layer has a thickness of between 100 nm and 10 μm, and preferably between 300 nm and 400 nm.

10. The chip as claimed in claim 7, comprising
at least one circuit in the cap; and/or
at least one circuit on the cap, connected to the cap by an inorganic $SiO_2$ matrix.

11. A plate having a thickness of between 200 μm and 1 mm and being connected to a layer of gel of inorganic silica, having a thickness of between 100 nm and 10 μm to form a chip as claimed in claim 7.

* * * * *